US012704474B2

(12) United States Patent
Shido et al.

(10) Patent No.: US 12,704,474 B2
(45) Date of Patent: Aug. 11, 2026

(54) GAS SENSOR USING IONIC LIQUID

(71) Applicant: Panasonic Intellectual Property Management Co., Ltd., Osaka (JP)

(72) Inventors: Chiaki Shido, Kyoto (JP); Atsuo Nakao, Nara (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 405 days.

(21) Appl. No.: 18/551,325

(22) PCT Filed: Mar. 16, 2022

(86) PCT No.: PCT/JP2022/011857
§ 371 (c)(1),
(2) Date: Sep. 19, 2023

(87) PCT Pub. No.: WO2022/202523
PCT Pub. Date: Sep. 29, 2022

(65) Prior Publication Data

US 2024/0183814 A1 Jun. 6, 2024

(30) Foreign Application Priority Data

Mar. 24, 2021 (JP) ................................ 2021-050522

(51) Int. Cl.
*G01N 27/12* (2006.01)
*G01N 33/00* (2006.01)

(52) U.S. Cl.
CPC ....... *G01N 27/125* (2013.01); *G01N 33/0027* (2013.01)

(58) Field of Classification Search
CPC ......................... G01N 27/125; G01N 33/0027
See application file for complete search history.

(56) References Cited

U.S. PATENT DOCUMENTS

| | | | | |
|---|---|---|---|---|
| 2008/0312365 | A1* | 12/2008 | Maton | C08G 77/14 524/588 |
| 2011/0226619 | A1 | 9/2011 | Eckhardt et al. | |
| 2013/0153442 | A1* | 6/2013 | Chen | G01N 27/407 205/789 |
| 2017/0212104 | A1* | 7/2017 | Schnorr | G01N 33/531 |

(Continued)

FOREIGN PATENT DOCUMENTS

| | | |
|---|---|---|
| JP | 2002-526769 A | 8/2002 |
| JP | 2010-175428 A | 8/2010 |

(Continued)

OTHER PUBLICATIONS

International Search Report dated Jun. 7, 2022 issued in International Patent Application No. PCT/JP2022/011857, with English translation.

(Continued)

*Primary Examiner* — Nathaniel J Kolb
(74) *Attorney, Agent, or Firm* — Rimon P.C.

(57) ABSTRACT

A gas sensor includes a sensitive portion and a plurality of electrodes arranged via the sensitive portion. The sensitive portion includes an ionic liquid and is configured to have electrical resistance that changes when the sensitive portion adsorbs a gas molecule. The ionic liquid preferably includes a hydrophobic anion. The hydrophobic anion preferably includes an organic fluorine compound. The organic fluorine compound preferably has a trifluoromethyl group.

14 Claims, 6 Drawing Sheets

(56) References Cited

U.S. PATENT DOCUMENTS

| | | | | |
|---|---|---|---|---|
| 2019/0079046 | A1* | 3/2019 | Zeng .................. | G01N 27/4045 |
| 2020/0033283 | A1 | 1/2020 | Nakao et al. | |

FOREIGN PATENT DOCUMENTS

| | | | |
|---|---|---|---|
| JP | 2012-510612 | A | 5/2012 |
| JP | 2014-006128 | A | 1/2014 |
| JP | 2017-521685 | A | 8/2017 |
| JP | 2018-112510 | A | 7/2018 |
| WO | 00/20852 | A1 | 4/2000 |
| WO | 2018/186268 | A1 | 10/2018 |

OTHER PUBLICATIONS

Zhu, X. et al., A paper-supported graphene ionic liquid array for e-nose application, Chem. Commun., 2016, vol. 52, pp. 3042-3045 & Supporting Information, DOI: 10.1039/c5cc08652c.

Park, C. H. et al., Ionic Liquid-Carbon Nanotube Sensor Arrays for Human Breath Related Volatile Organic Compounds, ACS Sensors, 2018, vol. 3, pp. 2432-2437, DOI: 10.1021/acssensors.8b00987.

Netto, Mariana M. O. et al., Biopolymer based ionogels as active layers in low-cost gas sensors for electronic noses, Sensors & Actuators: B. Chemical, 2020, vol. 315, 128025, https://doi.org/10.1016/j.snb.2020.128025.

Abu-Hani, Ayah F. S. et al., Design, fabrication, and characterization of low-power gas sensors based on organic-inorganic nanocomposite, Organic Electronics, 2017, vol. 42, pp. 284-292.

Li. Yan et al., Carbon black-ionic liquid gel for gas sensing, Chemical Research and Application, 2010, vol. 22, No. 5, pp. 625-628** with English abstract.

* cited by examiner

GAS SENSOR USING IONIC LIQUID

CROSS-REFERENCE OF RELATED APPLICATIONS

This application is the U.S. National Phase under 35 U.S.C. § 371 of International Patent Application No. PCT/JP2022/011857, filed on Mar. 16, 2022, which in turn claims the benefit of Japanese Patent Application No. 2021-050522, filed on Mar. 24, 2021, the entire disclosures of which Applications are incorporated by reference herein.

TECHNICAL FIELD

The present disclosure generally relates to a gas sensor, and more particularly relates to a gas sensor including a sensitive portion and a plurality of electrodes arranged via the sensitive portion.

BACKGROUND ART

Patent Literature 1 discloses a sensor. The sensor includes a region containing a conductive organic material and a region containing a conductive material having a different composition from the conductive organic material. The sensor provides an electrical path through the region containing the conductive organic material and the region containing the conductive material. The conductive organic material is selected from the group consisting of polyanilines, emeraldine salts of polyanilines, polypyrroles, polythiophenes, poly EDOTs, and their derivatives.

The sensor of Patent Literature 1 has so low a response speed that it sometimes takes a few minutes to have measurement done a single time.

CITATION LIST

Patent Literature

Patent Literature 1: JP 2002-526769 A

SUMMARY OF INVENTION

An object of the present disclosure is to provide a gas sensor with a high response speed.

A gas sensor according to an aspect of the present disclosure includes a sensitive portion and a plurality of electrodes arranged via the sensitive portion. The sensitive portion includes an ionic liquid and is configured to have electrical resistance that changes when the sensitive portion adsorbs a gas molecule.

DESCRIPTION OF EMBODIMENTS

First Embodiment (1) Overview

A gas sensor 1 according to an exemplary embodiment of the present disclosure may be implemented as, for example, an artificial olfactory sensor and may be used to, for example, detect odor molecules as detection target gas molecules. Examples of the odor molecules include volatile organic compounds (VOCs) and ammonia. The gas sensor 1 is used to detect VOCs as detection target gas molecules. The gas sensor 1 detects VOCs as odor gas molecules included in a sample gas such as a gas taken from a food, a breath taken from a human body, or the air taken from a building room. Note that the detection target gas molecules to be detected by the gas sensor 1 do not have to be VOCs but may also be multiple types of odor molecules including VOCs or non-odor molecules such as molecules of a flammable gas or a poisonous gas like carbon monoxide.

Figures 1A, 1B:
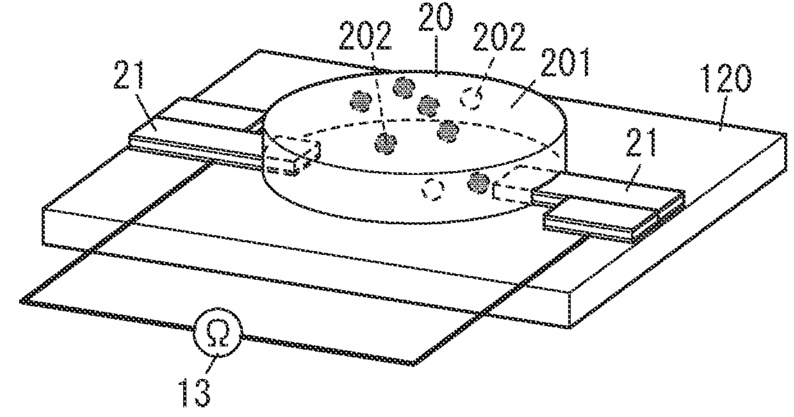
FIG. 1A is a plan view illustrating a gas sensor according to an exemplary embodiment.
FIG. 1B is a perspective view illustrating a sensitive portion of the gas sensor according to the exemplary embodiment.

FIG. 1A illustrates a gas sensor 1 according to this embodiment. This gas sensor 1 includes, on a substrate 120, at least one sensitive portion 20 and a plurality of electrodes 21. This gas sensor 1 includes a plurality of sensitive portions 20. With respect to each of these sensitive portions 20, a plurality of (e.g., a pair of) electrodes 21 are arranged via the sensitive portion 20. A number of sensitive portions 20 are arranged vertically and horizontally to form an array (e.g., a 4×4 array in this embodiment) of sensitive portions 20. Each of these sensitive portions 20 is formed in a circular pattern in plan view. Note that the number, arrangement, and shape of the sensitive portions 20 in the gas sensor 1 do not have to be the ones shown in FIG. 1A but may also be changed as appropriate according to the type of the gas sensor 1, for example.

As shown in FIG. 1B, each sensitive portion 20 includes a gas adsorbent 201 and conductive particles 202. The sensitive portion 20 is formed by dispersing a plurality of conductive particles 202 in the matrix of the gas adsorbent 201. Each electrode 21 is electrically connected to the conductive particles 202 in the gas adsorbent 201. In addition, the pair of electrodes 21 are also electrically connected to a detection unit in a processing unit 13.

The gas adsorbent 201 is formed to adsorb gas molecules G as detection target molecules. The gas adsorbent 201 also has electrical insulation properties and is formed out of a gas adsorbing material in the shape of a membrane, a plate, or a sheet. The gas adsorbing material as a constituent material for the gas adsorbent 201 includes an ionic liquid. An appropriate type of ionic liquid is selected according to, for example, the type of a chemical substance (gas) to be adsorbed by the gas adsorbent 201 and the type of the conductive particles 202.

The conductive particles 202 are particles with electrical conductivity. The sensitive portion 20 is made electrically conductive by including the plurality of conductive particles 202. The conductive particles 202 may include at least one material selected from the group consisting of carbon materials, conductive polymers, metals, metal oxides, semiconductors, superconductors, and complex compounds.

Figure 2A:
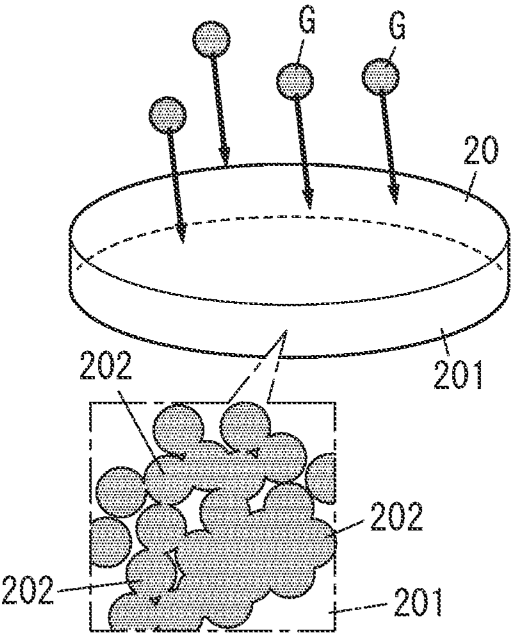
FIGS. 2A and 2B illustrate how a sensitive membrane of the gas sensor operates.
Figure 2B:
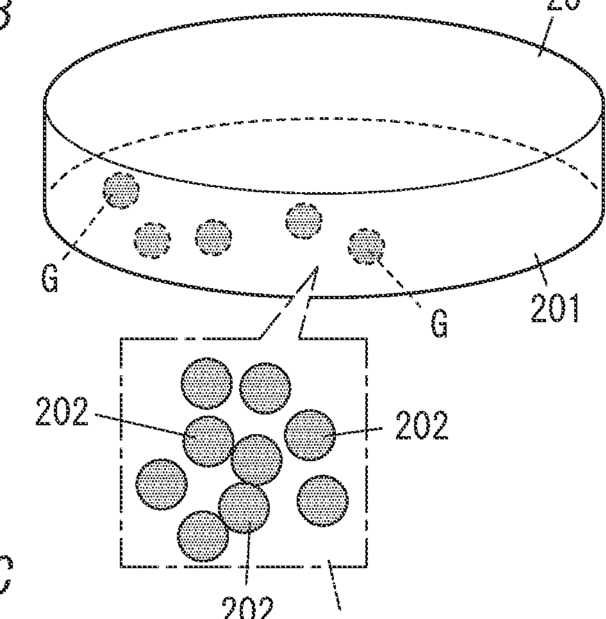
Figure 2C:
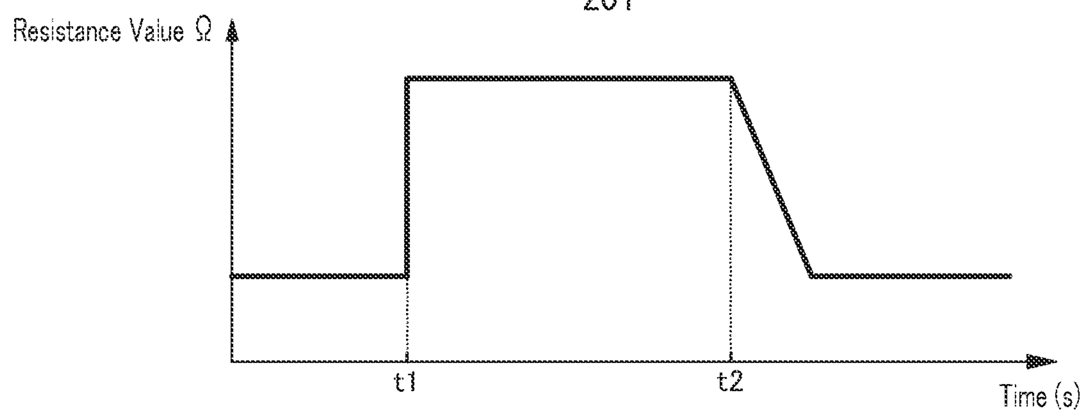
FIG. 2C is a graph showing how the resistance value may change with time through the operation of the sensitive membrane of the gas sensor.

In such a sensitive portion 20, the gas adsorbent 201 is less thick before adsorbing the gas molecules G as shown in FIG. 2A. That is to say, the plurality of conductive particles 202 are dispersed more densely in the gas adsorbent 201. Once the sensitive portion 20 has adsorbed the gas molecules G, the gas adsorbent 201 expands to have an increased thickness. That is to say, the plurality of conductive particles 202 are dispersed more sparsely in the gas adsorbent 201 as shown in FIG. 2B. As a result, the interval between the plurality of conductive particles 202 dispersed in the gas adsorbent 201 broadens, thus causing an increase in resistance value when the sensitive portion 20 adsorbs the gas molecules G at a time t1 as shown in FIG. 2C. Meanwhile, as the gas molecules G desorb from the sensitive portion 20, the gas adsorbent 201 of the sensitive portion 20 shrinks to have a decreased thickness (i.e., the state shown in FIG. 2A) from the expanded state (i.e., the state shown in FIG. 2B). As a result, the resistance value of the sensitive portion 20 gradually decreases since a time t2 when the gas molecules G start to desorb. The gas sensor 1 may determine, by making the detection unit of the processing unit 13, which is electrically connected to the electrodes 21, detect this change in the resistance value, whether there are any gas molecules G in the gas supplied such as the air.

(2) Details

As described above, the sensitive portion 20 of the gas sensor 1 according to this embodiment includes the gas adsorbent 201. The gas adsorbent 201 includes an ionic liquid. The ionic liquid is a salt (low molecular substance) which is liquid at an ordinary temperature and causes less steric hindrances than a high molecular substance that has been used for a sensitive portion of a gas sensor. That is why the gas molecules G as detection target molecules would be adsorbed into the gas adsorbent 201 easily and the gas molecules G adsorbed into the gas adsorbent 201 would have a high diffuse rate in the gas adsorbent 201. Consequently, this causes an increase in the response speed of the gas sensor 1. In addition, the gas adsorbent 201 including the ionic liquid also desorbs the gas molecules G at high speeds. Thus, the gas sensor 1 according to this embodiment may cause a significant structural change reversibly to the conductive particles by making the ionic liquid as the gas adsorbent of the sensitive portion 20 adsorb and desorb the gas molecules G at high speeds.

Besides, the ionic liquid has so low a vapor pressure as to vaporize hardly. This makes it easier to maintain the shape of the sensitive portion 20. Furthermore, the ionic liquid has so high stability that the chemical structure thereof changes less significantly and hardly deteriorates. Moreover, the ionic liquid may have its propertied changed when modified by any of various combinations of cations and anions or respective cations or anions. Thus, multiple different types of ionic liquids may be formed by $10^{16}$ different combinations of cations and anions. Therefore, if a plurality of gas adsorbents 201 are configured as respective combinations of multiple different types of cations and anions, it makes it easier for the plurality of gas adsorbents 201 to adsorb multiple different types of gas molecules G, which is advantageous to provide a gas sensor 1 with multi-channel capability. That is to say, this increases the selectivity of a desired type of gas molecules G as the detection target molecules for the gas sensor 1, thus enabling the type of the gas molecules G to be identified more accurately.

In this embodiment, examples of cation (species) of the ionic liquid include imidazolium (5-membered ring, conjugated), piperidinium (6-membered ring, single bond), pyrrolidinium (5-membered ring, single bond), pyridinium (6-membered ring, conjugated), ammonium, sulfonium, and phosphonium. In this embodiment, examples of anion (species) of the ionic liquid include a carboxylate ion, a phosphate ion, a sulfonate ion, a tetrafluoroboronate ion, a trifluoromethyl group ($[Tf2N]^-$, hydrophobic), a hexafluorophosphate ion, and trifluoromethanesulfonate ($[TfO]^-$, hydrophobic).

In this embodiment, the anion of the ionic liquid is preferably a hydrophobic anion. This reduces the chances of water being adsorbed into the gas adsorbent 201 of the sensitive portion 20, thus increasing the sensitivity of the gas sensor 1 to the gas molecules G as the detection target molecules. That is to say, the air includes not only the gas molecules G but also a lot of water molecules (water) as well. The water molecules have a far higher concentration than the gas molecules G, and therefore, a plenty of water molecules are easily adsorbed into the gas adsorbent 201. That is why water affects the detection result of the gas sensor 1 so significantly that it is difficult for gas sensor 1 to have good response to the gas molecules G as the detection target molecules. To overcome this problem, according to this embodiment, a hydrophobic anion is used as the ionic liquid of the gas adsorbent 201, thus reducing the chances of water molecules being adsorbed into the gas adsorbent 201 and thereby reducing the effect of water on the detection result of the gas sensor 1.

As used herein, to be "hydrophobic" would be substantially synonymous with having low hydrogen bond acceptability. Since the reactivity between water and the ionic liquid heavily depends on a hydrogen bond, the reactivity would be reduced by using an anion with a low degree of hydrogen bond acceptability as the anion of the ionic liquid. In that case, —OH produced by polarization of water is a hydrogen bond donor and N, O, F, and other atoms produced by polarization of the anion are hydrogen bond acceptors. The hydrophobic anion preferably has a hydrogen bond acceptability parameter (β value) less than 0.3, for example. The smaller the β value is, the less likely the anion forms a hydrogen bond to water. The lower limit of the β value is not limited to any particular value but only needs to be greater than zero.

As the hydrophobic anion, an organic fluorine compound is preferably used. This decreases the hydrogen bond acceptability of the hydrophobic anion, thus reducing the chances of water being adsorbed into the gas adsorbent 201. Also, the organic fluorine compound for use as the hydrophobic anion is preferably a compound having a trifluoromethyl group. This further decreases the hydrogen bond acceptability of the hydrophobic anion, thus further reducing the chances of water being adsorbed into the gas adsorbent 201. Specific examples of such a compound having a trifluoromethyl group include bis(trifluoromethanesulfonyl) amide ion (see the following chemical formula (1)). Note that the hydrophobic anion preferably has no carboxyl groups. This makes it easier for the hydrophobic anion to exhibit hydrophobicity.

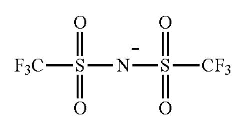

(1)

In this embodiment, imidazolium is preferably used as the cation of the ionic liquid. Moreover, it is preferable to use a highly hydrophobic cation such as imidazolium having an alkyl chain with seven or more carbon atoms. The imidazolium used in this embodiment is expressed by the following chemical formula (2):

(2)

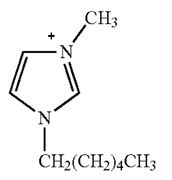

The ionic liquid that forms the gas adsorbent 201 may contain cations and anions at a constant ratio. For example, the ionic liquid may contain monovalent anions and cations at an equal ratio from the viewpoint of valence.

The sensitive portion 20 of the gas sensor 1 according to this embodiment includes a plurality of conductive particles 202. The plurality of conductive particles 202 are dispersed in the gas adsorbent 201. As the plurality of conductive particles 202, a carbon black, for example, is preferably used. In that case, the electrical resistance value of the sensitive portion 20 is particularly likely to change when the gas sensor 1 is exposed to a gas. Also, the conductive particles 202 preferably include an oxide semiconductor. The oxide semiconductor is preferably antimony tin oxide. This increases the chances of the electrical resistance value of the sensitive portion 20 changing particularly significantly when the gas sensor 1 is exposed to a gas.

The conductive particles 202 preferably have a mean particle size equal to or greater than 10 nm and equal to or less than 300 nm, for example. This increases the dispersibility of the conductive particles 202 in the gas adsorbent 201. The mean particle size of the conductive particles 202 is a number-based arithmetic mean particle size calculated based on an electron micrograph of the conductive particles 202.

The ratio of the conductive particles 202 contained in the sensitive portion 20 is not limited to any particular value. For example, the proportion of the conductive particles 202 is preferably 200 parts by mass with respect to 100 parts by mass of the gas adsorbent (ionic liquid) 201. That is to say, the ratio by mass of the conductive particles to the ionic liquid is preferably 2 to 1. This increases the chances of the electrical resistance of the sensitive portion 20 changing particularly significantly when the gas sensor 1 is exposed to a gas.

The gas sensor 1 according to this embodiment is formed with the plurality of sensitive portions 20 and the plurality of electrodes 21 provided on the substrate 120. A pair of electrodes 21 are in contact with, and electrically connected to, each of the sensitive portions 20. To manufacture the gas sensor 1, the plurality of sensitive portions 20 are formed on the substrate 120 on which the plurality of electrodes 21 have been formed. Each of the sensitive portions 20 may be formed by, for example, applying a molding material, containing the ionic liquid and the conductive particles, by a technique such as an inkjet method or a dispensing method.

(3) Variations

Note that the embodiment described above is only an exemplary one of various embodiments of the present disclosure and should not be construed as limiting. Rather, the exemplary embodiment may be readily modified in various manners depending on a design choice or any other factor without departing from the scope of the present disclosure.

In the exemplary embodiment described above, each sensitive portion 20 includes an ionic liquid with electrical insulation properties and conductive particles and is made electrically conductive by the conductive particles. However, this is only an example and should not be construed as limiting. Alternatively, the sensitive portion 20 may contain no conductive particles. In that case, the ionic liquid included in the gas adsorbent 201 has electrical conductivity. As the ionic liquid with electrical conductivity, an ionic liquid having any of various modification groups may be used, for example. Then, when the gas molecules as detection target molecules are adsorbed into the gas adsorbent 201, the gas adsorbent 201 expands, thus causing a change in the electrical resistance value of the sensitive portion 20 between the plurality of electrodes 21. The gas molecules G may be detected by measuring the change in the electrical resistance value.

Second Embodiment

A gas sensor 1 according to a second embodiment includes an ionic liquid having a different structure from the counterpart of the gas sensor 1 according to the first embodiment.

In the following description, any constituent element of this second embodiment, having the same function as a counterpart of the first embodiment described above, will be designated by the same reference numeral as that counterpart's, and description thereof will be omitted herein as appropriate.

Note that the configuration to be described below for the second embodiment may be adopted as appropriate in combination with the configuration that has been described for the first embodiment (including its variations).

In the first embodiment described above, to reduce the effect of water on the gas sensor 1, the anion of the ionic liquid of the gas adsorbent 201 is supposed to be a hydrophobic anion. On the other hand, according to this second embodiment, the anion of the ionic liquid of the gas adsorbent 201 includes a hydrophilic anion to increase the sensitivity of the gas sensor 1 to particular gas molecules G. As used herein, the hydrophilic anion only needs to have a higher degree of hydrogen bond acceptability than the hydrophobic anion used for the first embodiment and to be hydrophilic. Specifically, the hydrophilic anion is preferably an anion with a hydrogen bond acceptability parameter ($\beta$ value) equal to or greater than 0.3. The upper limit of the $\beta$ value is not limited to any particular value but may be, for example, equal to or less than 0.8.

As the hydrophilic anion, any anion other than an anion of an organic fluorine compound may be used. In particular, an anion with no trifluoromethyl groups may be used as the hydrophilic anion. Specific examples of hydrophilic anions include a halogen ion, a nitrate ion, a tetrafluoroborate ion, a hexafluorophosphate ion, a thiocyanate ion, an alkyl sulfate ion, a p-toluenesulfonate ion, and a tetrafluoro acetate ion. Among other things, a hexafluorophosphate ion ($PF_6^-$), which is a weakly hydrophilic anion, and a tetrafluoroborate ion ($BF_4^-$), which is more hydrophilic than $PF_6^-$, are preferably used.

Using a hydrophilic anion as an anion of the ionic liquid of the gas adsorbent 201 increases the chances of the gas molecules G, which are a hydrogen bond donor, being adsorbed to the gas adsorbent 201. This increases the sensitivity of the gas sensor 1 to the gas molecules G as a hydrogen bond donor. Specifically, if the gas molecules G are pyrrole molecules, the pyrrole molecules are more likely to be adsorbed into the gas adsorbent 201, thus increasing the detection sensitivity of the gas sensor 1 to the pyrrole molecules. Consequently, the gas sensor 1 may use a hydrophilic anion as an anion of the ionic liquid of the gas adsorbent 201 to increase the detection sensitivity to the gas molecules G as a hydrogen bond donor.

Note that as the cation of the ionic liquid, the same cation (e.g., imidazolium) as the one used in the first embodiment may also be used. According to this embodiment, using, in combination, the same cation and different anions makes it easier to prepare ionic liquids with different properties.

Third Embodiment

If a gas sensor 1 according to a third embodiment includes a plurality of sensitive portions 20, the ionic liquid included in the gas adsorbent 201 of each of the sensitive portions 20 has a different structure from the counterpart of the gas sensor 1 according to any of the first and second embodiments described above.

In the following description, any constituent element of this third embodiment, having the same function as a counterpart of the first or second embodiment described above, will be designated by the same reference numeral as that counterpart's, and description thereof will be omitted herein as appropriate.

Note that the configuration to be described below for the third embodiment may be adopted as appropriate in combination with the configuration that has been described for the first or second embodiment (including their variations).

When the gas sensor 1 according to this embodiment includes a plurality of sensitive portions 20, the respective gas adsorbents 201 of the sensitive portions 20 may be prepared using mutually different types of ionic liquids. This allows different types of gas molecules G to be adsorbed into the respective gas adsorbents 201 of the sensitive portions 20, thus increasing the detection sensitivity of the gas sensor 1 to multiple different types of gas molecules G and thereby making it easier to provide a gas sensor 1 with multi-channel capability.

For example, in some of the plurality of sensitive portions 20, the gas adsorbent 201 may be prepared using an ionic liquid including a hydrophobic anion. On the other hand, in others of the plurality of sensitive portions 20, the gas adsorbent 201 may be prepared using an ionic liquid including a hydrophilic anion. This makes it easier for the sensitive portions 20 including the gas adsorbent 201 containing the hydrophilic anion to selectively detect the gas molecules G of a hydrogen bond donor such as pyrrole, while making it easier for the sensitive portions 20 including the gas adsorbent 201 containing the hydrophobic anion to selectively detect gas molecules G of a non-hydrogen bond donor.

EXAMPLES

Figure 3:
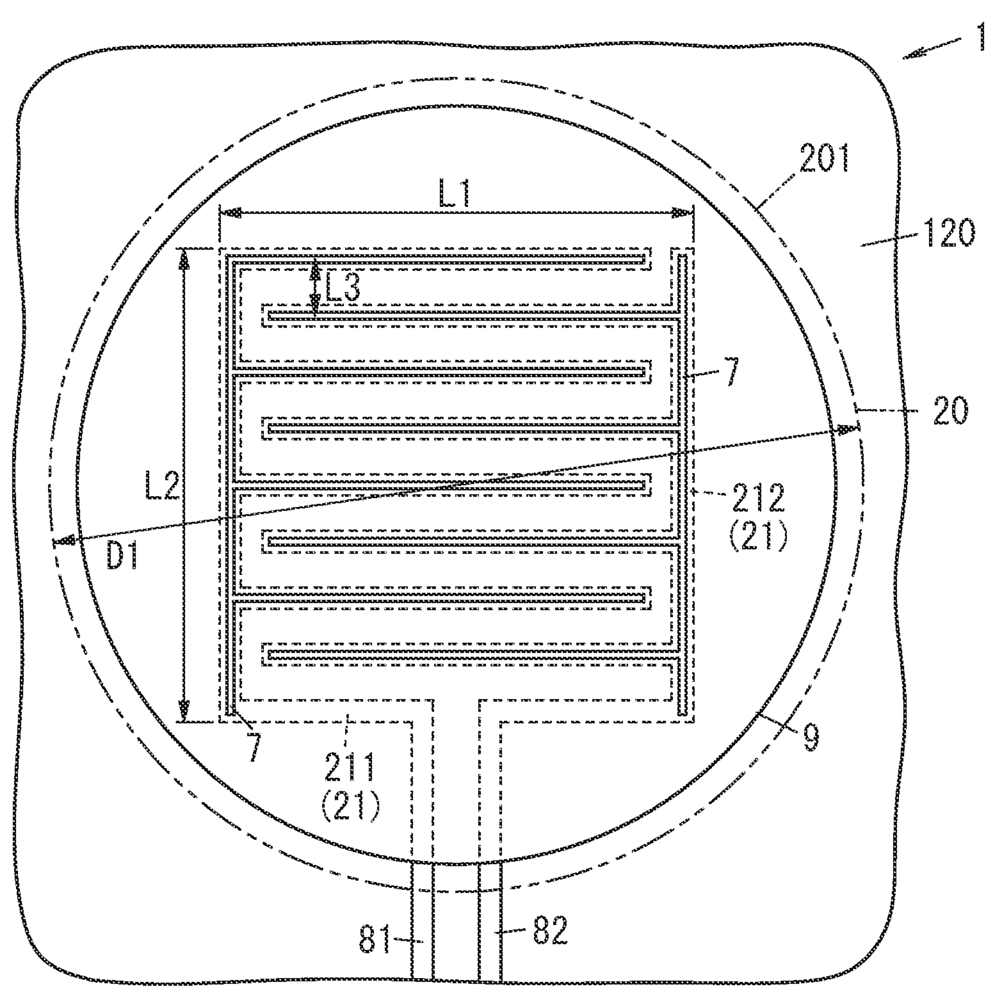
FIG. 3 is a schematic plan view illustrating a gas sensor under test.

The structure of a gas sensor 1 under test is schematically shown in FIG. 3. In this gas sensor 1, a first electrode 211 and a second electrode 212 were formed on a substrate 120 with electrical insulation properties to form a comb-tooth electrode pattern. The comb-tooth electrode pattern had a dimension L1 of 520 μm when measured along the comb teeth thereof and a dimension L2 of 500 μm when measured perpendicularly to the comb teeth. In addition, a film with electrical insulating properties (insulating film 9) was also provided over the substrate 120 to cover the first electrode 211 and the second electrode 212. Strip-shaped openings 7 each having a width of 5 μm were provided through the insulating film 9 to overlap with the first electrode 211 and the second electrode 212 as shown in FIG. 3. A dimension L3 between the respective centerlines of two adjacent openings 7 shown in FIG. 3 was 60 μm. Furthermore, a sensitive portion 20 including the gas adsorbent 201 and the conductive particles 202 was further formed over the substrate 120 to cover the insulating film 9 and to have a thickness of 1 μm. This allows the sensitive portion 20 to make contact with the first electrode 211 and the second electrode 212 through the openings 7. The sensitive portion 20 had a diameter D1 of 900 μm as shown in FIG. 3. In addition, the gas sensor 1 was further provided with a first terminal 81 extending from one end of the first electrode 211 to protrude out of the sensitive portion 20 and a second terminal 82 extending from one end of the second electrode 212 to protrude out of the sensitive portion 20.

With a constant voltage applied to between the first terminal 81 and second terminal 82, the gas sensor 1 was loaded into a nitrogen gas flow and then gas molecules G as detection target molecules were supplied as an additional gas into the gas flow for 15 seconds. During this process, the amount of current flowing between the first terminal 81 and the second terminal 82 was measured. The electrical resistance value of the sensitive portion 20 was calculated based on the amount of current thus measured.

First Example

As an ionic liquid as a constituent material for the gas adsorbent 201 of the gas sensor 1 under test, imidazolium, of which the cation is expressed by the chemical formula (2), was used. As the anion, the hydrophobic anion expressed by the chemical formula (1) was used. A carbon black having a mean particle size of 44 nm was used as the conductive particles 202. The ratio by mass of the conductive particles 202 to the gas adsorbent 201 in the sensitive portion 20 was 2 to 1.

First Comparative Example

A gas sensor 1 was formed in the same way as in the first example except that the gas adsorbent 201 of the gas sensor 1 under test was made of polysiloxane (product name SP-2330 manufactured by Sigma-Aldrich) as a high-molecular material.

Figure 4:
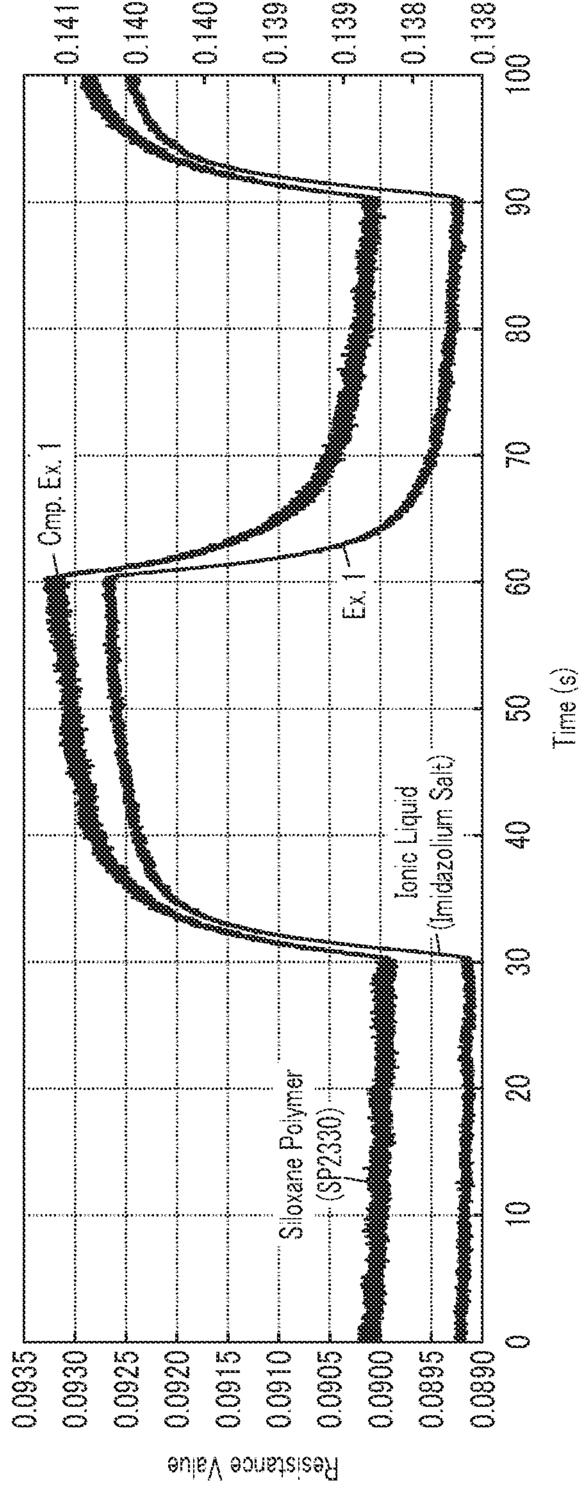
FIG. 4 is a graph showing a response curve of a gas sensor according to a first example.

The respective variations in the electrical resistance value of the sensitive portion 20 (i.e., the electrical resistance value measured between the first electrode 211 and the second electrode 212) with respect to the first example and the first comparative example are shown in FIG. 4. As the gas molecules G to be detected, benzaldehyde was used with its concentration set at 10 ppm.

Comparing the variations in electrical resistance value (response waveforms) of the first example and the first comparative example with each other, it can be seen that the waveform of the first example rises and falls more steeply than the waveform of the first comparative example. The gradients of the respective rising edges of the two waveforms were calculated by Ramer-Douglas-Peucker algorithm to be 0.89 with respect to the first example and 0.31 with respect to the first comparative example. The gradients of the respective falling edges of the two waveforms were calculated by the same algorithm to be 0.85 with respect to the first example and 0.29 with respect to the first comparative example. In the first example in which an ionic liquid was used for the sensitive portion 20, the gradients of the rising and falling edges were more than twice as steep as in the first comparative example in which a high molecular material was used. Consequently, it can be said that the first example achieved a higher response speed than the first comparative example.

Second Example

As an ionic liquid as a constituent material for the gas adsorbent 201, imidazolium, of which the cation is expressed by the chemical formula (2), was used. As the anion, a weakly hydrophilic hexafluorophosphate ion ($PF_6^-$) was used. In the other respects, the gas sensor 1 was formed in the same way as in the first example described above.

With respect to the first and second examples and the first comparative example, the sensitivities of the gas sensor 1 under test were measured when an evaluation gas, including benzaldehyde as the detection target gas molecules G at a concentration of 10 ppm, was used and when the air at a humidity of 30% was used as an evaluation gas. The sensitivity may be defined as Rs/R0, where Rs is the resistance value measured by the sensitive portion 20 when the evaluation gas is introduced into the gas sensor 1 and R0 is the resistance value measured by the sensitive portion 20 when an odorless gas (nitrogen gas) is introduced into the gas sensor 1.

Figure 5:
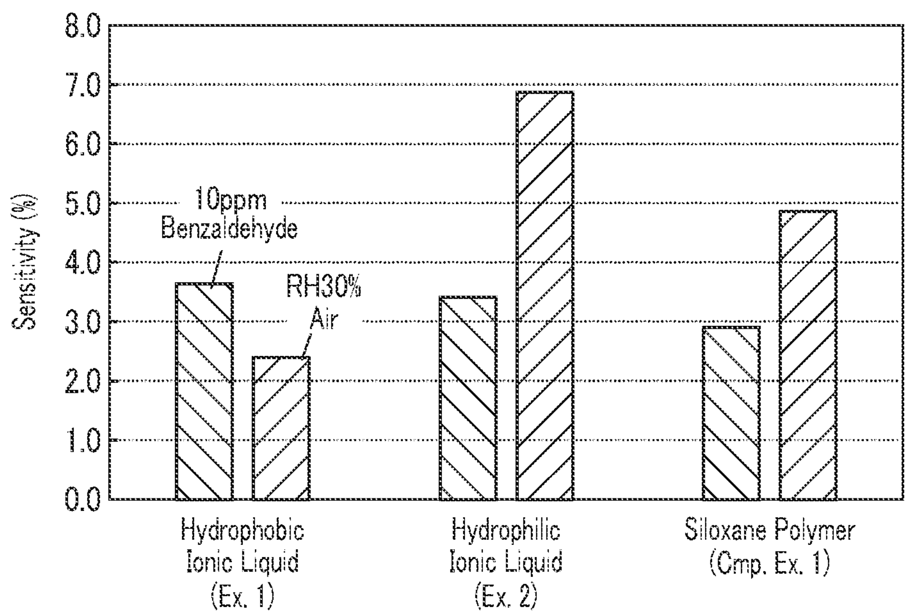
FIG. 5 is a graph showing respective sensitivities of gas sensors according to first and second examples and a first comparative example.

As shown in FIG. 5, it can be seen that in the first example, the sensitivity to benzaldehyde is higher than the sensitivity to water. It can also be seen that in the second example and the first comparative example, the sensitivity to water is higher than the sensitivity to benzaldehyde. Thus, it can be said that using a hydrophobic ionic liquid including a hydrophobic anion as the ionic liquid included in the gas adsorbent 201 may reduce the reactivity to water while maintaining the sensitivity to the VOC (benzaldehyde).

Third Example

As an ionic liquid as a constituent material for the gas adsorbent 201, imidazolium, of which the cation is expressed by the chemical formula (2), was used. As the anion, a hydrophilic tetrafluoroborate ion ($BF_4^-$) was used. In the other respects, the gas sensor 1 was formed in the same way as in the first example described above.

With respect to the first to third examples and the first comparative example, the sensitivities of the gas sensor 1 under test were measured when an evaluation gas, including nonanal as the detection target gas molecules G at a concentration of 2 ppm, was used, when an evaluation gas including benzaldehyde as the detection target gas molecules G at a concentration of 2 ppm was used, and when an evaluation gas including pyrrole as the detection target gas molecules G at a concentration of 2 ppm was used. The sensitivities were obtained in the same way as described above.

Figure 6:
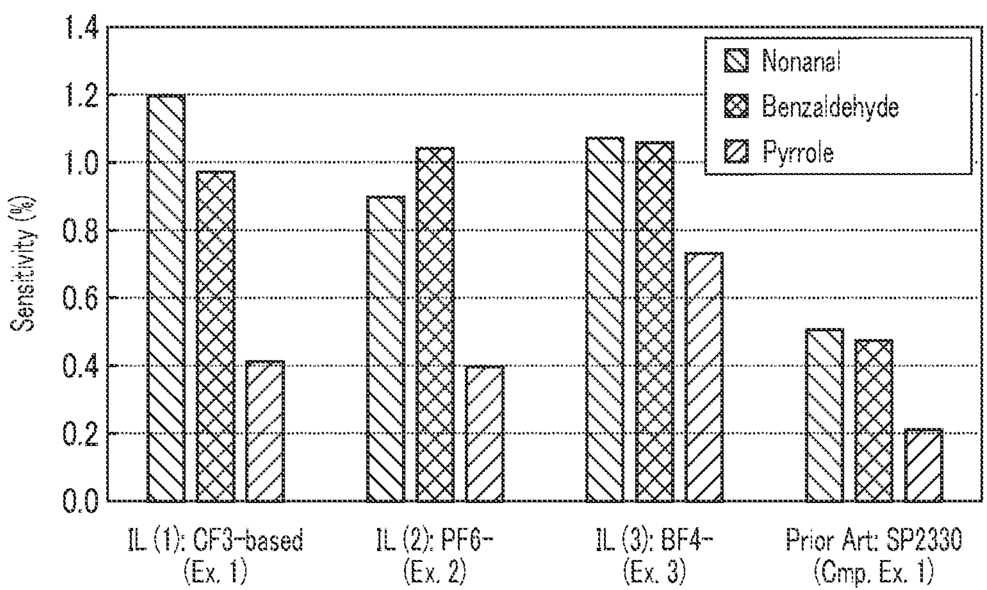
FIG. 6 is a graph showing respective sensitivities of gas sensors according to first to third examples and the first comparative example.

As shown in FIG. 6, the sensitivity of low-polarity molecules to pyrrole was low in the first and second examples and the first comparative example, while the sensitivity to pyrrole was higher in the third example than in any of the first and second examples and the first comparative example. Consequently, it can be said that using a hydrophilic ionic liquid including a highly hydrophilic $BF_4^-$ ion as the ionic liquid included in the gas adsorbent 201 enables detecting pyrrole at a high sensitivity.

(Recapitulation)

As can be seen from the foregoing description, a gas sensor (1) according to a first aspect includes a sensitive portion (20) and a plurality of electrodes (21) arranged via the sensitive portion (20). The sensitive portion (20) includes an ionic liquid and is configured to have electrical resistance that changes when the sensitive portion (20) adsorbs a gas molecule (G).

This aspect allows the sensitive portion (20) to adsorb and desorb the gas molecules (G) more quickly, thus causing an increase in the response speed of the gas sensor (1).

In a gas sensor (1) according to a second aspect, which may be implemented in conjunction with the first aspect, the sensitive portion (20) includes conductive particles (202) and is made electrically conductive by the conductive particles (202).

This aspect allows the sensitive portion (20) to adsorb and desorb the gas molecules (G) more quickly, and therefore, causes the sensitive portion (20) to change its electrical resistance value at a higher rate due to the presence of the conductive particles (202), thus causing an increase in the response speed of the gas sensor (1).

In a gas sensor (1) according to a third aspect, which may be implemented in conjunction with the first or second aspect, the ionic liquid includes a hydrophobic anion.

This aspect reduces the responsivity of the sensitive portion (20) to water, thus causing an increase in the detection sensitivity to the gas molecules (G) as a detect target.

In a gas sensor (1) according to a fourth aspect, which may be implemented in conjunction with the third aspect, the hydrophobic anion includes an organic fluorine compound.

This aspect further reduces the responsivity of the sensitive portion (20) to water, thus causing a more significant increase in the detection sensitivity to the gas molecules (G) as a detection target.

In a gas sensor (1) according to a fifth aspect, which may be implemented in conjunction with the fourth aspect, the organic fluorine compound has a trifluoromethyl group.

This aspect further reduces the responsivity of the sensitive portion (20) to water, thus causing a more significant increase in the detection sensitivity to the gas molecules (G) as a detection target.

In a gas sensor (1) according to a sixth aspect, which may be implemented in conjunction with the first aspect, the ionic liquid includes a hydrogen bond acceptor anion.

This aspect increases the adsorptivity of hydrogen bond donor gas molecules G to the sensitive portion (20), thus causing an increase in the detection sensitivity to the hydrogen bond donor gas molecules (G).

In a gas sensor (1) according to a seventh aspect, which may be implemented in conjunction with any one of the first to sixth aspects, a cation of the ionic liquid includes imidazolium.

This aspect stabilizes the properties of the sensitive portion (20), thus causing an increase in the detection sensitivity to the gas molecules (G).

A gas sensor (1) according to an eighth aspect, which may be implemented in conjunction with any one of the first to seventh aspects, includes a plurality of sensitive portions (20) respectively including ionic liquids of mutually different types. The plurality of sensitive portions (20) are arranged to form an array.

According to this aspect, the type of the gas molecules (G), to which the sensitive portion (20) is highly responsive, varies from one of the plurality of sensitive portions (20) to another, thus providing a gas sensor (1) with a multi-channel capability of detecting multiple types of gas molecules (G).

In a gas sensor (1) according to a ninth aspect, which may be implemented in conjunction with the eighth aspect, the plurality of sensitive portions (20) are respectively configured as an ionic liquid including a hydrophobic anion and an ionic liquid including a hydrophilic anion.

This aspect provides a gas sensor (1) having a high response speed and exhibiting high detection sensitivity to hydrogen bond donor gas molecules (G).

In a gas sensor (1) according to a tenth aspect, which may be implemented in conjunction with any one of the second to ninth aspects, the conductive particles (202) are a carbon black.

This aspect stabilizes the properties of the sensitive portion (20), thus causing an increase in the detection sensitivity to the gas molecules (G).

In a gas sensor (1) according to an eleventh aspect, which may be implemented in conjunction with any one of the second to tenth aspects, the conductive particles (202) include an oxide semiconductor.

This aspect stabilizes the properties of the sensitive portion (20), thus causing an increase in the detection sensitivity to the gas molecules (G).

In a gas sensor (1) according to a twelfth aspect, which may be implemented in conjunction with the eleventh aspect, the oxide semiconductor is antimony tin oxide.

This aspect stabilizes the properties of the sensitive portion (20), thus causing an increase in the detection sensitivity to the gas molecules (G).

In a gas sensor (1) according to a thirteenth aspect, which may be implemented in conjunction with the first aspect, the ionic liquid has electrical conductivity.

This aspect allows the sensitive portion (20) to adsorb and desorb the gas molecules (G) more quickly, thus causing an increase in the response speed of the gas sensor (1).

REFERENCE SIGNS LIST

1 Gas Sensor

20 Sensitive Portion

202 Conductive Particle

21 Electrode

G Gas Molecule

The invention claimed is:

1. A gas sensor comprising:

a sensitive portion; and a plurality of electrodes arranged via the sensitive portion, wherein:

the sensitive portion includes an ionic liquid and is configured to have electrical resistance that changes when the sensitive portion adsorbs a gas molecule, the sensitive portion includes conductive particles and is made electrically conductive by the conductive particles, and a ratio by mass of the conductive particles to the ionic liquid in the sensitive portion is 2 to 1.

2. The gas sensor of claim 1, wherein the ionic liquid includes a hydrophobic anion.

3. The gas sensor of claim 2, wherein the hydrophobic anion includes an organic fluorine compound.

4. The gas sensor of claim 3, wherein the organic fluorine compound has a trifluoromethyl group.

5. The gas sensor of claim 1, wherein the ionic liquid includes a hydrogen bond acceptor anion.

6. The gas sensor of claim 1, wherein a cation of the ionic liquid includes imidazolium.

7. The gas sensor of claim 1, comprising a plurality of sensitive portions respectively including ionic liquids of mutually different types, wherein the plurality of sensitive portions are arranged to form an array.

8. The gas sensor of claim 7, wherein the plurality of sensitive portions are respectively configured as an ionic liquid including a hydrophobic anion and an ionic liquid including a hydrophilic anion.

9. The gas sensor of claim 1, wherein the conductive particles are carbon black.

10. The gas sensor of claim 1, wherein the conductive particles include an oxide semiconductor.

11. The gas sensor of claim 10, wherein the oxide semiconductor is antimony tin oxide.

12. The gas sensor of claim 1, wherein the ionic liquid has electrical conductivity.

13. The gas sensor of claim 1, wherein the ionic liquid includes an anion, the anion has a hydrogen bond acceptability parameter less than 0.3.

14. The gas sensor of claim 1, wherein the ionic liquid includes an anion, the anion has a hydrogen bond acceptability parameter equal to or greater than 0.3 and equal to or less than 0.8.

* * * * *